United States Patent [19]

Boyadzhian et al.

[11] 4,056,563
[45] Nov. 1, 1977

[54] METHOD OF PRODUCING ALLYLACETATE

[76] Inventors: Varazdat Karapetovich Boyadzhian, ulitsa Grachia Nersesiana, 10, kv. 1; Saribek Saakovich Khachatrian, ulitsa Agaiana, 10, kv. 1-a; Genrikh Gevorkovich Stepanian, ulitsa Olega Koshevogo, 5, kv. 75; Volodya Karapetovich Eritsian, Achapniak, 11, kvartal 6, kv. 35; Edik Stepanovich Agavelian, ulitsa Grachia Kochara, 12, kv. 6, all of Erevan; Oleg Matveevich Nefedov, ulitsa Shukhova, 5/7, kv. 15, Moscow; Igor Evgenievich Dolgy, ulitsa Vernadskogo, 95, korpus 2, kv. 262, Moscow; Mikhail Fedorovich Sisin, ulitsa Schepkina, 30, kv. 12, Moscow; Alexei Yakovlevich Kolbasin, Salavat, bulvar Matrosova, 8/12, kv. 17; Ivan Konstantinovich Anikeev, Salavat, ulitsa Kalinina, 38, kv. 70, both of Bashkirskaya ASSR, all of U.S.S.R.

[21] Appl. No.: 653,375

[22] Filed: Jan. 28, 1976

[30] Foreign Application Priority Data

Jan. 31, 1975   U.S.S.R. .............................. 2101054

[51] Int. Cl.$^2$ ............................................ C07C 67/05
[52] U.S. Cl. ................................. 560/245; 252/431 C
[58] Field of Search ................................... 260/497 A

[56] References Cited

U.S. PATENT DOCUMENTS 3,609,180   9/1971   Shigenatsu ...................... 260/497 A

*Primary Examiner*—James O. Thomas, Jr.
*Assistant Examiner*—Michael Shippen

[57] ABSTRACT

A method of producing allylacetate residing in that propylene is reacted with acetic acid and oxygen in a gaseous phase at a temperature of 150°–250° C under a pressure of 1–10 atg in the presence of a catalyst containing tetraammonium palladium acetate of the formula / Pd(NH$_3$)$_4$ / (CH$_3$COO)$_2$ and activators on a support.

The proposed invention makes it possible to increase the yield of allylacetate per liter of the catalyst per hour.

2 Claims, No Drawings

METHOD OF PRODUCING ALLYLACETATE

The present invention relates to producing unsaturated esters of carboxylic esters and more particularly to a method of producing allylacetate which can be used as a starting material in chemical and petrochemical industries for preparing various products of organic synthesis as well as a range of polymer materials.

Known in the art is a method of producing allylacetate by oxyacetylation of propylene with acetic acid and oxygen in a gaseous phase at a temperature from 150°-250° C under a pressure of 1-10 atg in the presence of a catalyst containing a palladium salt, for example, palladium acetate, and activators on a support, mainly, aluminium oxide or silicic acid.

Salts of bismuth, copper, vanadium, sodium, potassium and other metals are used as activators. The process is carried out both in a stationary and in a fluidized bed of a catalyst.

The yield of allylacetate per litre of a catalyst per hour is 430-495 g/l.hr when the process is run in a stationary bed of a catalyst.

In case the process is conducted in a fluidized bed of a catalyst, the yield of allylacetate is 790 g/l.hr.

The principal disadvantage of the known methods is a low yield of allylacetatate per litre of a catalyst per hour due to poor efficiency of the catalyst.

The object of the invention is to increase the yield of allylacetate.

Said object is accomplished in a method of producing allylacetate by oxyacetylation of propylene with acetic acid and oxygen in a gaseous phase at a temperature from 150°-250° C under a pressure of 1-10 atg in the presence of a catalyst containing a palladium salt and activators on a support, according to the invention, as a palladium salt use being made of a complex salt thereof, namely, tetraamonium palladium acetate of the formula / Pd(NH$_3$)$_4$ /(CH$_3$COO)$_2$.

To increase the yield of allylacetate it is expedient to use a catalyst containing 1-10 wt % of tetraammonium palladium acetate.

To increase the catalyst efficiency it is preferable to use a mixture of zinc acetate and sodium acetate with copper acetylacetonate or copper acetate as activators.

The proposed method is realized as follows.

A vapour-gas mixture of propylene, acetic acid, and oxygen is passed through a reactor loaded with a catalyst at 150°-250° C and 1-10 atg. Said vapour gas mixture is condensed after leaving the reactor with subsequent isolation of the desired product.

The process is run in a stationary bed of the catalyst.

The catalyst contains tetraammonium palladium acetate in an amount of 1-10% of the total weight of the catalyst, 2.5 wt% of copper acetylace tonate or copper acetate, and 10 wt% of a mixture of zinc and sodium acetates in a ratio of 1:1 on a support, aluminium oxide thermally treated at 900° C being used as the support.

The catalyst is prepared in the following way. A 20% solution of NH$_3$ is added to an aqueous solution of tetraammonium palladium acetate up to pH = 12. The solution temperature is raised to 40°-50° and then copper acetylacetonate or copper acetate, sodium acetate, and zinc acetate are dissolved in succession in said solution at 40°-50° with stirring. The impregnation of aluminium oxide with the resulting solution is performed at 50° C. The support is kept in said solution for 4 hours, after which excess solution is decanted and the wet catalyst is dried at 85°-90° under a residual pressure of 300-350 mm Hg to a moisture content of 1%.

The use of tetraammonium palladium acetate as the main component of the catalyst increases the yield of allylacetate per litre of the catalyst per hour up to 2,180 g/l.hr due to enhancing the catalyst efficiency.

For a better understanding of the present invention specific examples of realizing the proposed method are given hereinbelow by way of illustration.

EXAMPLE 1

250 ml of a catalyst containing 2.0 wt % of tetraammonium palladium acetate, 2.5 wt % of zinc and sodium acetates in a 1:1 ratio deposited on aluminium oxide are put into a reactor. A vapour-gas mixture containing 3,000 nl/hr of propylene, 200 nl/hr of oxygen, and 800 g/hr of acetic acid is passed through the catalyst at 210° C under 5 atg. The vapour-gas mixture leaving the reactor is condensed and rectified. The yield of allylacetate is 1,435 g per litre of the catalyst per hour.

EXAMPLE 2

250 ml of a catalyst containing 10.0 wt % of tetraammonium palladium acetate, 2.5 wt % of copper acetylacetonate, and 10 wt % of a mixture of zinc and sodium acetates in a 1:1 ratio deposited on aluminium oxide are put into a reactor. A vapour-gas mixtureof propylene, oxygen, and acetic acid in amounts as described in Example 1 is passed through the catalyst at 210° under 5 atg.

The yield of allylacetate is 1,560 g per litre of the catalyst per hour.

EXAMPLE 3

250 ml of a catalyst containing 4.2 wt% of tetraammonium palladium acetate, 2.5 wt % of copper acetylacetonate, and 10 wt % of a mixture of zinc and sodium acetates in a 1:1ratio deposited on aluminium oxide are put into a reactor. A vapour-gas mixture containing propylene, acetic acid, and oxygen in amounts as described in Example 1is passed through the catalyst.

The yield of allylacetate is 1,135 g per litre of the catalyst per hour.

EXAMPLE 4

250 ml of a catalyst the composition of which is similar to that described in Example 3 are put into a reactor. A vapour-gas mixture containing 3,000 nl/hr of propylene, 200 nl/hr of oxygen, and 800 g hr of acetic acid is passed through the catalyst at 210° C under 6 atg.

The yield of allylacetate is 1,845 g per litre of the catalyst per hour.

EXAMPLE 5

250 ml of a catalyst the composition of which is similar to that described in Example 3 are put into the reactor. A vapour-gas mixture having the composition similar to that described in Example 4 is passed through the catalyst at 210° under 7 atg.

The yield of allylacetate is 2,180 g per litre of the catalyst per hour.

EXAMPLE 6

250 ml of a catalyst the composition of which is similar to that described in Example 3 are put into the reactor. A gas mixture containing 3,000 nl/hr of propylene, 200 nl/hr of oxygen, and 800 g/hr of acetic acid is passed through the catalyst.

The yield of allylacetate is 2,020 g per litre of the catalyst per hour.

EXAMPLE 7

250 ml of a catalyst containing 4.2 wt % of tetraammonium palladium acetate, 2.5 wt% of copper acetate, and 10 wt % of a mixture of zinc and sodium acetates in a 1:1 ratio are put into a reactor.

A mixture of propylene, acetic acid, and oxygen in amounts similar to those described in Example 6 is passed through the catalyst at 190° under 5 atg.

The yield of allylacetate is 1,180 g per litre of the catalyst per hour.

EXAMPLE 8

250 ml of a catalyst containing 10 wt % of tetraammonium palladium acetate, 2.5 wt % of copper acetate, and 10 wt % of a mixture of zinc and sodium acetates in a 1:1 ratio is put into a reactor. A mixture of propylene, oxygen, and acetic acid in amounts similar to those described in Example 6 is passed through the catalyst at 210° under 5 atg. The yield of allylacetate is 1,530 g per litre of the catalyst per hour.

What is claimed is:

1. A method of producing allylacetate by oxyacetylation of propylene residing in that propylene is reacted with acetic acid and oxygen in a gaseous phase at a temperature of 150°–250° C under a pressure of 1–10 atg in the presence of the catalyst tetraammonium palladium acetate of the formula $(CH_3COO)_2$ containing sodium acetate, zinc acetate and copper acetylacetonate or copper acetate on an alumina support.

2. A method as claimed in claim 1, wherein said catalyst contains 1–10 wt % of tetraammonium palladium acetate.

* * * * *